United States Patent [19]
Shin et al.

[11] Patent Number: 5,436,241
[45] Date of Patent: Jul. 25, 1995

[54] TOPICAL ANTI-INFLAMMATORY COMPOSITIONS CONTAINING PIROXICAM

[75] Inventors: Chung Shin, Livingston, N.J.; Luc Bossuyt, Trumbull, Conn.

[73] Assignee: Bristol-Myers Squibb Company, New York, N.Y.

[21] Appl. No.: 181,510

[22] Filed: Jan. 14, 1994

[51] Int. Cl.$^6$ .............................................. A61K 31/54
[52] U.S. Cl. .............................. 514/226.5; 514/224.2; 514/663; 514/667; 514/669
[58] Field of Search ........................... 514/224.2, 226.5

[56] References Cited

U.S. PATENT DOCUMENTS

| | | | |
|---|---|---|---|
| 3,591,584 | 7/1971 | Lombardino | |
| 4,582,831 | 4/1986 | Robertson | 514/225 |
| 4,678,666 | 7/1987 | Nozawa et al. | 424/81 |
| 4,994,457 | 2/1991 | Crawford et al. | 514/226.5 |
| 5,081,118 | 1/1992 | Braisted et al. | 514/226.5 |

Primary Examiner—José G. Dees
Assistant Examiner—Dwayne G. Jones
Attorney, Agent, or Firm—Morton S. Simon

[57] ABSTRACT

The composition contains: an antiinflammatory effective amount of piroxicam; an amount of tetrahydroxypropylethylenediamine sufficient to solubilize the piroxicam in the composition; an amount of $C_2$–$C_6$ alkylene glycol, or mixture thereof, sufficient to detackify the composition and provide humectancy; about 0.2% to about 2% carbomer; about 30% to about 60% $C_2$–$C_4$ alkanol; and water qs to 100%. Hydroxypropylcellulose can be added to the composition.

18 Claims, No Drawings

TOPICAL ANTI-INFLAMMATORY COMPOSITIONS CONTAINING PIROXICAM

BACKGROUND OF THE INVENTION

This invention relates to new and useful compositions containing an effective anti-inflammatory concentration of piroxicam in a dermatologically acceptable gel base. Clear compositions can be made and are preferred.

Although piroxicam is very active as an anti-inflammatory drug, it is sparingly soluble in water and is not oil soluble. To get the maximum efficacy that piroxicam can provide, the drug should be in solution.

When piroxicam is suspended in conventional dermatological bases, such as ointments or creams, it is poorly absorbed through the skin and does not afford maximum therapeutic efficacy. Alcoholic solutions of piroxicam would seem to offer a possible solution. However, when alcoholic solutions of piroxicam are applied to the skin, the alcohol evaporates off causing the piroxicam to precipitate onto the skin surface. The piroxicam precipitate is not absorbed through the skin.

In the presence of water, piroxicam converts to a hydrate. Since the hydrate is less soluble than piroxicam itself, it gradually crystallizes out. This not only reduces the penetration of piroxicam through the skin, but also impairs the stability of the product as well as its ability to form a film on the skin.

A similar problem occurs when a piroxicam containing gel is applied directly to sweating skin. The polymer gel-forming agent in the product salts out causing the gel to agglomerate on the skin instead of forming a continuous film. This is cosmetically inelegant. The agglomerates have an unpleasant feel. Moreover, piroxicam contained in such agglomerates is not readily bioavailable and efficacy of the product is greatly reduced. U.S. Pat. No. 4,678,666 discloses a piroxicam gel containing lower alkanol, water, carboxyvinyl polymer, polyhydric alcohol, alkanolamine and a film-forming agent. Patentees claim that their composition has excellent skin-permeability and none of the defects heretofore described. They employ alkanolamines such as monoalkanolamine, dialkanolamine and trialkanolamine to solubilize the piroxicam. Patentees also disclose that hydroxypropylcellulose was ineffective when combined with their piroxicam-ethanolamine solubilized compositions.

Although U.S. Pat. No. 4,678,666 teaches that alkanolamines are highly effective in increasing the solubility of piroxicam, the present inventor has found that clear-gel piroxicam containing formulations can not be produced when triethanolamine is employed as a solublizer and less than 30% by weight of water is present in the formulation. The product that results turns hazy and eventually forms two layers. Consequently, the gel compositions of U.S. Pat. No. 4678666, particularly those employing triethanolamine as a solubilizer, are less than satisfactory when such compositions contain less than 30% by weight of water.

The present inventor has discovered a new piroxicam solubilizer. The new solubilizer, tetrahydroxypropyl ethylenediamine, is not an alkanolamine as taught by U.S. Pat. No. 4678666. Moreover, it is superior to alkanolamines with respect to color, clarity and gel formation. Its use enables one skilled in the art to prepare stable piroxicam clear gel formulations containing less than 30% by weight of water.

Surprisingly, contrary to the teaching of U.S. Pat. No. 4,678,666 with compositions containing piroxicam solubilized by tetrahydroxypropyl ethylenediamine in accordance with the present invention, hydroxypropylcellulose, a material disclosed by Patentees in U.S. Pat. No. 4,678,666 to be unsatisfactory, is not only effective, it is preferred.

SUMMARY OF THE INVENTION

The present invention provides novel anti-inflammatory dermatologic gel compositions which, in their preferred form, have excellent clarity. The compositions of the instant invention are non-tacky and pleasant to use. It has been surprisingly found that by combining an anti-inflammatory effective amount of piroxicam with the water-soluble alkaline base tetrahydroxypropyl ethylenediamine, and solvents, gel forming agents, and an appropriate amount of film-forming agent (particularly, hydroxypropyl cellulose), one can produce an anti-inflammatory dermatologic gel composition that has excellent clarity, good stability and is pleasant to use. Counter-irritants such as menthol, eugenol, methyl salicylate, etc., can optionally be included as components of the present piroxicam gel composition.

The present inventor has discovered that when gel forming agents, such as Carbomer 940 or 980, are combined with a thickening agent, such as hydroxypropyl cellulose, and with solvents such as various glycols and triols, anti-inflammatory piroxicam containing gel compositions can be produced. Such compositions possess good stability, are cosmetically elegant and surprisingly exhibit no balling or salting out when the gel product is applied to sweating skin. Moreover, compositions having excellent clarity can be produced.

It should be noted that the present invention is not limited to clear gel systems. Once piroxicam is solubilized in water with tetrahydroxypropyl ethylenediamine, the solubilized piroxicam can be incorporated into an oil-in-water emulsion system, a water-in-oil emulsion system or a gel system.

It should be further noted that where used in the present specification and claims, unless indicated to the contrary, percentage is percent by weight, based on the total weight of the composition.

DETAILED DESCRIPTION OF THE INVENTION

As stated heretofore, the composition of the present invention contains an anti-inflammatory effective amount of piroxicam. The piroxicam is generally present in the composition in from about 0.3% to about 2%. Preferably it is present from about 0.75% to about 1.5%.

The composition also contains, as an essential component, an amount of tetrahydroxypropyl ethylenediamine sufficient to solubilize the piroxicam in the composition. Generally the tetrahydroxypropyl ethylenediamine is present in an amount from about 2% to about 4%. Preferably it is present in an amount of from about 2.5% to about 3.5%.

The composition also contains, as an essential component a $C_2$–$C_4$ alkanol. Ethanol is preferred. The alkanol is generally present in an amount of from about 30% to about 60%. Preferably in an amount of from about 35% to 55%. The alcohol serves to dissolve alcohol soluble ingredients which may be optionally added to the composition. Water is another essential ingredient. It is present in an amount sufficient to bring the composition to 100%. The water serves to dissolve the hydroxypropylcellulose (if present), the carbomer and other water soluble components.

The composition further contains, as an essential component a humectant-detackifier selected from the group consisting of $C_2$–$C_6$ alkylene glycol or diols, $C_3$–$C_6$ alkylene triols, and mixtures thereof. The preferred triol is glycerin. Preferred $C_2$–$C_6$ alkylene glycols or diols include propylene glycol, butylene glycol, hexylene glycol, dipropylene glycol and mixtures thereof. A mixture of propylene glycol, dipropylene glycol and glycerin is preferred. Most preferred is a mixture of propylene glycol, dipropylene glycol and glycerin in the respective ratio of 3:2: 2.5. The humectant-detackifier is present in the composition in an amount sufficient to reduce tack and provide humectancy to the skin. Generally, the humectant-detackifier is present in an amount of from about 5% to about 20%. Preferably, it is present in an amount of from about 10% to 15%.

To form a gel, the composition also requires the presence of Carbomer. Carbomer is generally present in an amount of about 0.2% to about 2%. Preferably it is present in an amount of from about 0.5% to about 1.5%. Carbomers 940 and 980 are preferred.

The compositions of the present invention may contain an additional gelling agent such as hydroxypropyl cellulose. In point of fact, compositions of the present invention that contain hydroxypropyl cellulose are preferred. When present, hydroxypropyl cellulose is employed in an amount of from about 0.25% to about 1%. Preferably it is present in an amount of from about 0.5% to about 0.75%.

Examples of other ingredients that can optionally be included in the gel composition of the instant invention are menthol, eugenol, methyl salicylate and camphor. Preservatives, perfume agents, colors and like ingredients typically contained in dermatological formulations may also be included. If the composition contains sufficient alcohol there may be no need for a preservative.

In U.S. Pat. No. 4,678,666 patentees teach that hydroxypropyl cellulose is ineffective when combined with piroxicam ethanolamine solubilized compositions. In other words, patentees teach that hydroxypropyl cellulose was unsatisfactory.

Contrary to this teaching, the present inventor has found that with compositions containing piroxicam solubilized by tetrahydroxypropyl ethylenediamine, hydroxypropyl cellulose is not only effective, it is preferred.

This is clearly seen from the Examples which follow, particularly Examples 2, 4 and 5. Examples 6 and 7 also demonstrate this. Example 7 is a comparative example wherein piroxicam was solubilized by triethanolamine as taught by U.S. Pat. No. 4,678,666. Example 6 is an example in accordance with the present invention in that piroxicam was solubilized by tetrahydroxypropyl ethylenediamine. The compositions of Examples 6 and 7 each contained 0.5% hydroxypropyl cellulose. The formulation of Example 6 was a clear gel. The formulation of Example 7 was hazy and showed separation.

Examples 6 & 7 demonstrate that when the solubilizer of the present invention is employed one can surprisingly make clear stable piroxicam gels containing hydroxypropyl cellulose, a material taught by patentees in U.S. Pat. No. 4,678,666 to be unsuitable.

The instant invention will be more fully appreciated from the Examples which follow. They are offered to illustrate the scope of the invention and are not intended to limit same. In these Examples unless indicated otherwise, all percentages are percent by weight (% w/w) and are based on the total weight of the composition.

EXAMPLE 1

Anti-inflammatory Clear Gel

| Ingredient | % |
| --- | --- |
| L-Menthol | 5.43 |
| Eugenol | 1.37 |
| Methyl salicylate | 10.20 |
| Alcohol (anhydrous) | 38.50 |
| Tetrahydroxypropyl ethylenediamine | 2.00 |
| Piroxicam | 0.50 |
| Carbomer 940 | 1.00 |
| Water (purified) | 31.00 |
| Propylene glycol | 6.00 |
| Dipropylene glycol | 4.00 |
| | 100.00 |

The above formulation was prepared as follows:

(a) The menthol, eugenol and methyl salicylate were dissolved in 13 parts of the alcohol with the aid of a Lightnin' mixer.

(b) The tetrahydroxypropyl ethylenediamine was dissolved in an equal weight of water. Then half of the solution prepared in Step (a) was added thereto.

(c) The piroxicam was added to the solution prepared in Step (b).

(d) In a separate container, the Carbomer 940 was dispersed in a solution containing the propylene glycol, the dipropylene glycol and the remaining alcohol and water. The remaining tetrahydroxypropyl ethylenediamine was added and the resultant mixture was mixed well.

(e) The solution prepared in Step (c) was then mixed with the gel prepared in Step (d). Sufficient alcohol was added to adjust for weight loss due to evaporation.

The resultant product was a clear gel having a viscosity at ambient temperature of 21,750 cps±2,000 cps (Brookfield Viscometer) and a pH of 7.0±0.2

EXAMPLE 2

Anti-inflammatory Clear Gel

| Ingredient | % |
| --- | --- |
| L-Menthol | 5.43 |
| Eugenol | 1.37 |
| Methyl salicylate | 10.20 |
| Alcohol (anhydrous) | 38.50 |
| Tetrahydroxypropyl ethylenediamine | 2.00 |
| Piroxicam | 0.50 |
| Water (purified) | 25.50 |
| Glycerin | 5.00 |
| Propylene glycol | 6.00 |
| Dipropylene glycol | 4.00 |
| Carbomer 980 | 1.00 |
| Hydroxypropyl cellulose | 0.50 |
| | 100.00 |

The above formulation was prepared as described in Example 1 except that hydroxypropyl cellulose and glycerin were added to the hydroalcoholic Carbomer 980 base.

The resultant clear gel had at ambient temperature a viscosity of 25,250 cps±2,000 cps (Brookfield Viscometer) and a pH of 7.2±0.2.

EXAMPLE 3

Anti-inflammatory Clear Gel

| Ingredient | % |
| --- | --- |
| L-Menthol | 5.43 |
| Eugenol | 1.37 |
| Methyl salicylate | 10.20 |
| Alcohol (anhydrous) | 37.20 |
| Tetrahydroxypropyl ethylenediamine | 3.00 |
| Piroxicam | 0.50 |
| Water (purified) | 25.50 |
| Glycerin | 5.00 |
| Propylene glycol | 6.00 |
| Dipropylene glycol | 4.00 |
| Carbomer 980 | 1.30 |
| Hydroxypropyl cellulose | 0.50 |
| | 100.00 |

The above formulation was prepared as described in Example 1.

The resultant clear gel had at ambient temperature a viscosity of 24,900 cps±2,000 cps and a pH of 7.3±0.2.

The following Examples 4 and 5 compare the new solubilizer, tetrahydroxypropyl ethylene diamine, to the alkanolamines taught by U.S. Pat. No. 4,678,666.

EXAMPLES 4 AND 5

Topical Anti-inflammatory Compositions

| Ingredient | % Ex.4 | % Ex.5 |
| --- | --- | --- |
| L-Menthol | 5.43 | 5.43 |
| Eugenol | 1.37 | 1.37 |
| Methyl salicylate | 10.20 | 10.20 |
| Alcohol (anhydrous) | 37.20 | 37.20 |
| Tetrahydroxypropyl ethylenediamine | 3.00 | — |
| Triethanolamine | — | 3.00 |
| Piroxicam | 0.50 | 0.50 |
| Water (purified) | 25.50 | 25.50 |
| Glycerin | 5.00 | 5.00 |
| Propylene glycol | 6.00 | 6.00 |
| Dipropylene glycol | 4.00 | 4.00 |
| Carbomer 980 | 1.30 | 1.30 |
| Hydroxypropyl cellulose | 0.50 | 0.50 |
| | 100.00 | 100.00 |

The above compositions were prepared as described in Example 1.

Example 4 yielded a clear gel having at ambient temperate a viscosity of 15,500 cps±2,000 cps (Brookfield Viscometer) and a pH of 7.2±0.2

Example 5 yielded a hazy liquid which separated into two layers. It had at ambient temperature a viscosity of 75 cps±10 cps (Brookfield Viscometer) and a pH of 7.3±0.2.

Example 5 shows that when triethanolamine is employed to solubilize piroxicam a gel cannot be produced when the composition contains less than 30% by weight of water or about 37% by weight of alcohol.

EXAMPLES 6 AND 7

Topical Anti-inflammatory Compositions

| Ingredient | % Ex.6 | % Ex.7 |
| --- | --- | --- |
| Alcohol (anhydrous) | 54.20 | 54.20 |
| Tetrahydroxypropyl ethylenediamine | 2.50 | — |
| Triethanolamine | — | 2.50 |
| Piroxicam | 0.50 | 0.50 |
| Water (purified) | 26.00 | 26.00 |
| Glycerin | 5.00 | 5.00 |
| Propylene glycol | 6.00 | 6.00 |
| Dipropylene glycol | 4.00 | 4.00 |
| Carbomer 980 | 1.30 | 1.30 |
| Hydroxypropyl cellulose | 0.50 | 0.50 |
| | 100.00 | 100.00 |

The above compositions were prepared as described in Example 1.

In Example 6, the product was a clear gel having at ambient temperature a viscosity of 27,500 cps±2,000 cps (Brookfield Viscometer) and a pH of 7.3±0.2.

In Example 7, the product was a hazy liquid exhibiting two separate layers. The product had a viscosity of 30 cps (Brookfield Viscometer) and a pH of 7.5±0.2.

Comparative Examples 6 and 7 show that when triethanolamine is used to solubilize piroxicam, a gel cannot be formed in the presence of less than 30% water or in the presence of higher than about 54% alcohol.

What is claimed is:

1. A composition comprising:
   (i) an anti-inflammatory effective amount of piroxicam;
   (ii) an amount of tetrahydroxypropyl ethylene-diamine sufficient to solubilize the piroxicam in the composition;
   an amount of $C_2-C_6$ alkylene glycol or mixture thereof, sufficient to detackify the composition and provide humectancy thereto;
   (iv) from about 0.2% to about 2% carbomer;
   (v) from about 30% to about 60% of a $C_2-C_4$ alkanol; and
   (vi) water to bring the composition to 100%.

2. The composition as claimed in claim 1, wherein the piroxicam is present in an amount of from about 0.3% to about 2%.

3. The composition as claimed in claim 1, wherein the piroxicam is present in an amount of from about 0.75% to about 1.5%.

4. The composition as claimed in claim 1, wherein the tetrahydroxypropyl ethylenediamine is present in an amount from about 2% to about 4%.

5. The composition as claimed in claim 1, wherein the tetrahydroxypropylethylenediamine is present in an amount from about 2.5% to about 3.5%.

6. The composition as claimed in claim 1, further including from about 0.25% to about 1% hydroxypropyl cellulose.

7. The composition as claimed in claim 6, wherein the hydroxypropyl cellulose is present in an amount of from about 0.5% to about 0.75%.

8. The composition as claimed in claim 1, wherein the alkanol is present in an amount of from about 35% to about 55%.

9. The composition as claimed in claim 1, wherein the $C_2-C_6$ alkylene glycol is propylene glycol, butylene glycol, hexylene glycol, dipropylene glycol, glycerin or a mixture thereof.

10. The composition as claimed in claim 9, wherein the mixture is propylene glycol, dipropylene glycol and glycerin in the respective ratio of 3:2:2.5.

11. The composition as claimed in claim 1, wherein the alkylene glycol is present in an amount of about 5% to about 20%.

12. The composition as claimed in claim 11, wherein the alkylene glycol is present in an amount of about 10% to about 15%.

13. The composition as claimed in claim 1, wherein the carbomer is present in an amount of from about 0.5% to about 1.5%.

14. The composition as claimed in claim 1, wherein the carbomer is Carbomer 940 or Carbomer 980.

15. The composition as claimed in claim 1, further including a counterirritant selected from the group consisting of menthol, eugenol, methyl salicylate, camphor and mixtures thereof.

16. The composition as claimed in claim 1, wherein the composition is a clear gel.

17. A composition comprising piroxicam and an amount of tetrahydroxypropyl ethylenediamine sufficient to solubilize the piroxicam.

18. A method of solubilizing piroxicam comprising mixing the piroxicam with an amount of tetrahydroxypropyl ethylenediamine sufficient to solubilize the piroxicam.

* * * * *